United States Patent
Hahmann et al.

(10) Patent No.: US 6,858,137 B2
(45) Date of Patent: Feb. 22, 2005

(54) FILTER MODULE HAVING A CLOSURE ELEMENT

(75) Inventors: Uwe Hahmann, Bad Homburg (DE); Christian Sauerwald, St. Wendel (DE); Klaus Heilmann, St. Wendel (DE); Gerhard Breith, Pirmasens (DE); Steffen Fritzsche, Tholey (DE)

(73) Assignee: Fresenius Medical Care Deutschland GmbH (DE)

( * ) Notice: Subject to any disclaimer, the term of this patent is extended or adjusted under 35 U.S.C. 154(b) by 0 days.

(21) Appl. No.: 10/052,768

(22) Filed: Jan. 18, 2002

(65) Prior Publication Data

US 2002/0104791 A1 Aug. 8, 2002

Related U.S. Application Data

(63) Continuation of application No. 09/441,182, filed on Nov. 15, 1999, now Pat. No. 6,419,825.

(30) Foreign Application Priority Data

Nov. 13, 1998 (DE) .......................................... 198 52 557

(51) Int. Cl.[7] .......................... A61M 39/20; B01D 61/30
(52) U.S. Cl. ...................... 210/232; 210/235; 215/247; 604/91; 604/167.01; 604/256
(58) Field of Search .................................. 210/232, 235, 210/450; 215/247; 604/91, 256, 167.01, 321, 411

(56) References Cited

U.S. PATENT DOCUMENTS

| | | | | |
|---|---|---|---|---|
| 4,143,853 A | * | 3/1979 | Abramson | 251/149.1 |
| 4,197,848 A | * | 4/1980 | Garrett et al. | |
| 4,387,879 A | * | 6/1983 | Tauschinski | 251/149.1 |
| 4,475,548 A | * | 10/1984 | Muto | 604/167 |
| 4,511,359 A | * | 4/1985 | Vaillancourt | 604/411 |
| 4,769,017 A | * | 9/1988 | Fath et al. | 604/83 |
| 4,929,235 A | * | 5/1990 | Merry et al. | 604/167 |
| 5,328,041 A | * | 7/1994 | Hook et al. | 215/247 |
| 5,474,544 A | * | 12/1995 | Lynn | 251/349 |
| 5,797,897 A | * | 8/1998 | Jepson et al. | 604/412 |
| 5,817,043 A | * | 10/1998 | Utterberg | 604/4 |
| 5,957,898 A | * | 9/1999 | Jepson et al. | 604/256 |
| 5,971,181 A | * | 10/1999 | Niedospial, Jr. et al. | 215/247 |
| 6,039,718 A | * | 3/2000 | Niedospial, Jr. | 604/408 |

FOREIGN PATENT DOCUMENTS

| | | | |
|---|---|---|---|
| DE | 2817102 | * | 10/1979 |
| DE | 3322003 | * | 12/1984 |
| DE | 4303026 | * | 8/1994 |
| EP | 0269152 | * | 6/1988 |
| EP | 0352540 | * | 11/1989 |
| EP | 0352540 | * | 1/1990 |

* cited by examiner

*Primary Examiner*—John Kim
(74) *Attorney, Agent, or Firm*—Kenyon & Kenyon

(57) ABSTRACT

A closure element for sterile closure of connections, in particular connections of filter modules for dialysis, hemofiltration or ultrafiltration is described. A closure element with a simple design that provides a reliable seal is formed by having the closure element include a wall with an automatically closing slit-shaped indentation which when closed creates a germ-proof seal. The sealing element is used for sterile closure of connections of medical items, as well as for the medical items themselves.

14 Claims, 5 Drawing Sheets

FILTER MODULE HAVING A CLOSURE ELEMENT

RELATED APPLICATION

This application is a continuation of Applicants' U.S. patent application Ser. No. 09/441,182, filed Nov. 15, 1999, U.S. Pat. No. 6,419,825, which is incorporated by reference herein as fully as if set forth in its entirety.

The present invention relates to a closure element for the sterile closure of connections, and in particular to the closure of connections with filter modules for dialysis, hemofiltration or ultrafiltration.

DESCRIPTION OF RELATER ART

In the production of filter modules for dialysis, it is necessary to sterilize the filter modules after the actual manufacturing process and also to protect the filter modules from external influences, such as the penetration of microorganisms or dirt. One method of sterilizing filter modules is the so-called in-line sterilization, where the interior areas of the filter module are cleaned, although the outside is not sterilized. Because open contact of the connections of the filter module during or after the sterilization step must absolutely be avoided, the filter module must be sealed in such a way that no contamination or soiling of the interior of the filter module can occur during sterilization or after removal from the sterilization device.

European Patent 352,540 describes a generic closure element consisting of two parts, with the first part of the closure element being attached to the connection of the filter module or the dialyzer, while the second part of the closure element is accommodated in a receptacle space of the first closure element part. The device is arranged movably between an open position and a closed position in this receptacle space. Thus, in the open position, passage of the sterilization medium and sterilization of all sealing surfaces and guidance surfaces can be achieved. In the closed position, reliable sealing of the dialyzer can be achieved. Although such a closure element guarantees reliable sealing of the filter module, it has the disadvantage of having a relatively complex structure.

SUMMARY OF THE INVENTION

The present invention is an improvement upon a generic closure element having a simple design that can reliably ensure a sterile closure.

The closure element includes a wall having a slit-shaped indentation that closes automatically, and when closed forms a germ-proof closure. There are also fastening means that are adjacent to the wall, so the closure element can be attached to a connection by these fastening means. Such a closure element according to this invention has a simple design and provides a reliable and sterile seal of a medical object, such as a filter module, during and after sterilization, due to the automatically closing slit-shaped indentation. When a suitable connecting element such as a connection of a sterilization device or of a dialysis machine is inserted, the slit-shaped indentation in the closure element according to this invention is opened to fit the shape of the connecting element.

When the connecting element according to this invention is removed from the closure element, after sterilization or treatment, the slit-shaped indentation closes automatically, thus preventing contamination of the sterilized area as well as leakage from the item sealed with the closure element.

In an especially advantageous embodiment, the closure element has an essentially cylindrical shape, and the fastening means are formed by the cylindrical surface and the slit-shaped indentation, arranged on one of the end faces of the cylinder. The closure element forms a germ-proof connection to the medical item by means of the cylindrical surface. Such a cap-like design of the closure element has the advantage that the fluid supplied and removed flows along a simple linear path in a passage through the closure element. The development of dead zones can thus be effectively prevented by an appropriate arrangement of the slit-shaped indentation. This design also prevents the mixing of different fluids, such as mixtures containing different active ingredients or medicines, that pass through the closure element.

Another embodiment of the present invention provides for a symmetrical closure element design. Such a design not only simplifies the manufacture of the closure element, but also permits simple handling as well as simple attachment and use of the closure element on the corresponding connection of a filter module.

A preferred embodiment of the present invention provides for the slit-shaped indentation to have the shape of a cross or a star. This shape permits a very good flexibility and adaptation to connections of various shapes and various diameters, in comparison with a simple linear design of the indentation. Another wall having an opening for the passage of a fluid may be provided opposite to the wall with the indentation. In one example, the middle of the indentation may be aligned with the opening.

Another embodiment of this invention provides for the surface of the other wall extending around the opening to extend in a plane essentially perpendicular to the joining direction of the connecting element of the invention. In this case, the closure element according to this invention additionally provides a tight connection of the connecting element, for example between a dialysis machine and the filter module. A seal can be achieved by the connecting element having its end face sealably placed inside the opening of the other wall.

It is especially advantageous if the closure element according to this invention is a single piece, to provide advantages in the manufacturing process.

It is also especially advantageous if the wall with the indentation, and more preferably advantageous if the entire closure element, is made of plastic. In this manner, the flexibility and elasticity of the closure element can be varied widely through the choice of a suitable plastic. In addition, compatibility with the fluid used or with a mixture containing various active ingredients can be achieved through the choice of the plastic. The use of plastic for the wall of the closure element having the indentation, or for the entire closure element, also has the advantage that a simple and cost-effective manufacturing process can produce a variety of different embodiments and designs of the closure element. It is especially advantageous if the plastic is a silicone plastic.

An advantageous embodiment includes a wall with the slit-shaped indentation in the closure element that has a spring element acting in the radial direction. This yields the advantage that radial stress forces are reduced over the transverse direction in the path of the spring element. This results in a slit-shaped indentation in the wall having improved sealing properties.

In another embodiment of the present invention, the spring element can be formed by recesses that alternate or are individually placed on the top and/or bottom sides of the wall. The recesses may be partially circular.

It is especially advantageous if no spring element is provided in the areas of the wall extending in the longitudinal direction of the slit-shaped indentation. This design increases the radial force acting in the direction of the slit, which yields an especially tight closure of the slit-shaped indentation.

Another embodiment of the present invention provides for the slit-shaped indentation in the closure element to form a germ-proof closure resisting up to a pressure difference of about ±0.25 bar.

The present invention also concerns the use of a closure element for the sterile closure of connections of medical items. In a preferred embodiment, the medical item is a filter module for dialysis, hemofiltration or ultrafiltration, with the closure element being used for in-line sterilization of the filter module.

Another embodiment of the present invention provides for fastening means of the closure element that permit the closure element to be placed on projecting connections, or inserted into bushing-like connections.

The present invention also concerns a medical item with one or more connections for supplying and/or removing a fluid, with at least one connection being provided with a closure element according to this invention. The medical item may be a filter module for dialysis, hemofiltration or ultrafiltration.

It is especially advantageous if the closure element is designed in such a way that its inside surface is connected by a germ-proof connection to the outer surface of a projecting connection. It is also advantageous if the outside surface of the closure element is connected by a germ-proof connection to the inside surface of a bushing-shaped connection.

Another embodiment of the present invention provides for at least two connections of the medical item having a closure element according to this invention.

BRIEF DESCRIPTION OF THE DRAWING

Additional details and advantages of the present invention will now be explained in greater detail on the basis of embodiments illustrated in the figures. In the drawings.

DETAILED DESCRIPTION OF THE PREFERRED EMBODIMENTS OF THE INVENTION

Figures 1A, 1B:
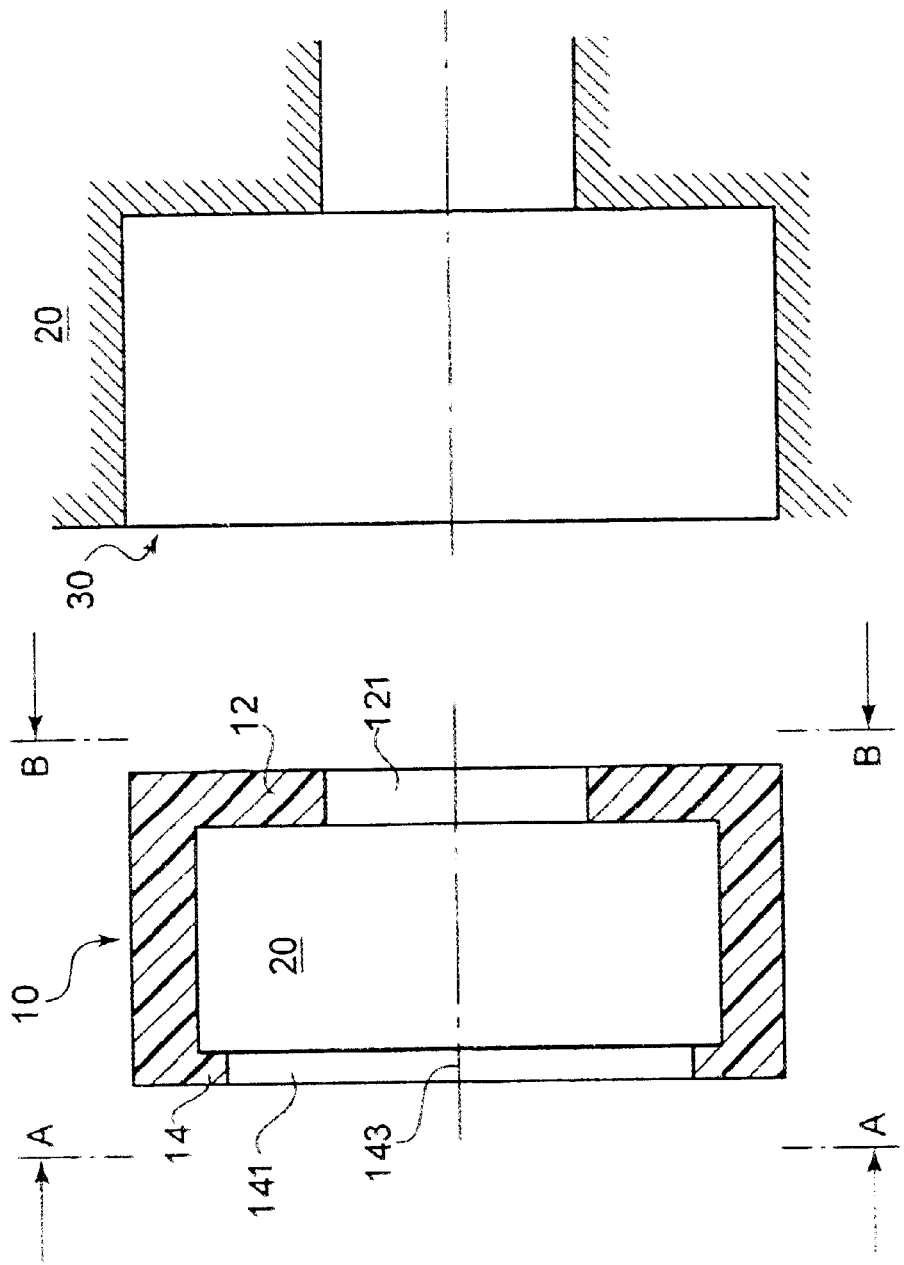
FIGS. 1A and 1B: are longitudinal sections respectively through a first embodiment of a closure element according to this invention, and through a corresponding recess in the housing to accommodate the closure element.

FIG. 1 shows closure element 10, according to this invention, with walls 12 and 14 being parallel. Both walls 12, 14 border a hollow cylindrical space 20, which is also defined by the cylindrical surfaces which are connected to walls 12, 14 and serve as fastening means. Walls 12 and 14 are adjacent to the cylindrical surfaces of closure element 10, and meet it at a right angle.

Wall 14 has slit-shaped, automatically closing indentation 141 with a central section 143. Wall 12 has a central opening 121 of circular shape. Opening 121 and central section 143 of indentation 141 in wall 14 are aligned with one another, so that the present closure element can be used to connect linear connecting elements.

FIG. 1B shows a housing 20 having an opening 30, for example of a filter module, for accommodating closure element 10 according to this invention. Opening 30 preferably is cylindrical, and can accommodate closure element 10 in a form-fitting manner. To achieve a reliable seating of the closure element 10 in the housing recess 30, the outside diameter of closure element 10 preferably is slightly greater than the inside diameter of the housing recess 30. This also produces a reliable and germ-proof seal between the housing 20 and closure element 10.

Figure 2B:
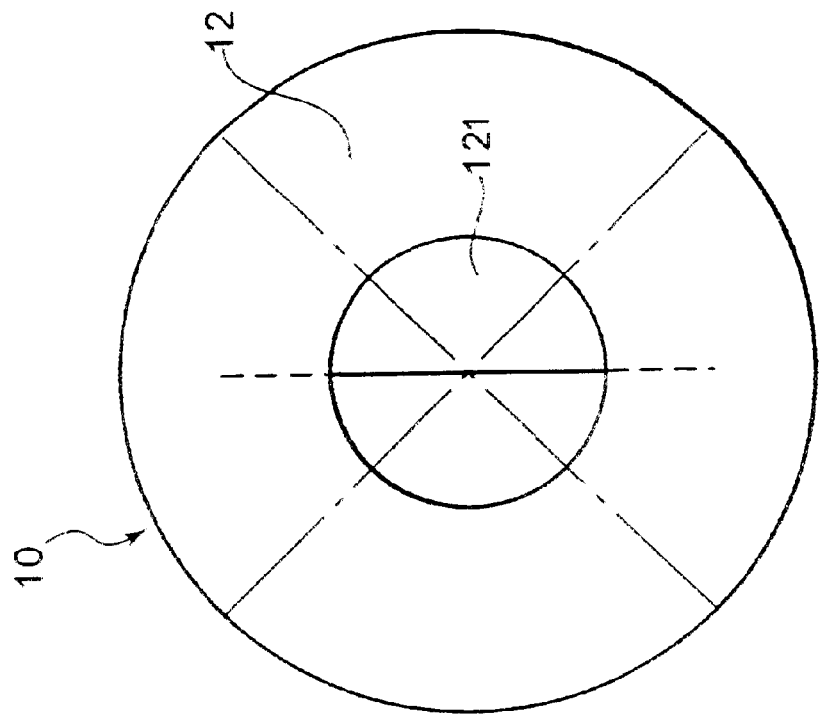
FIGS. 2A and 2B: show sectional views respectively of the closure element from FIGS. 1A and 1B, according to perspective A—A and perspective B—B.
Figure 2A:
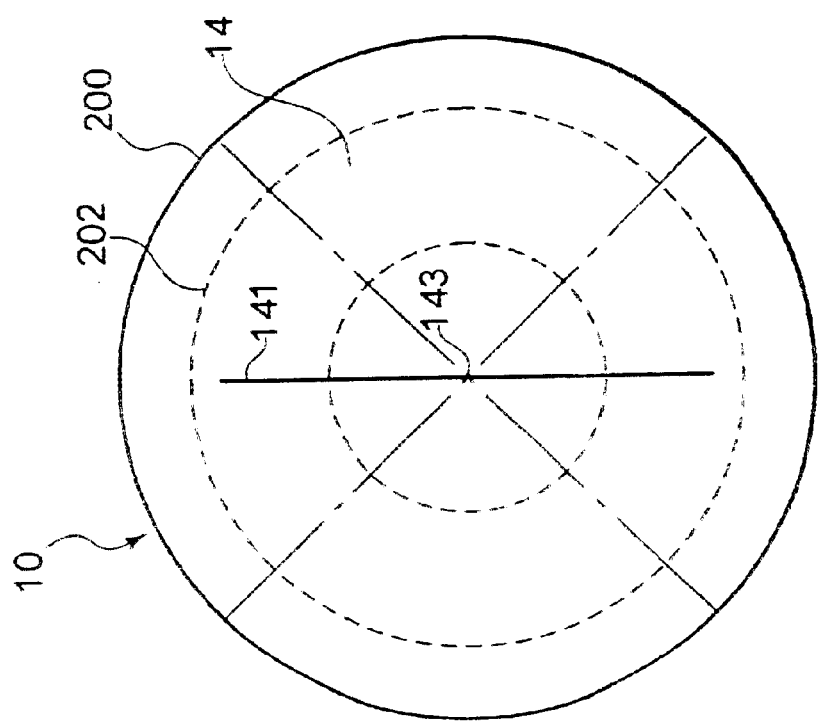

FIG. 2 shows two views of sealing element 10 according to this invention, seen from perspectives A—A (FIG. 2A) and B—B (FIG. 2B) of FIG. 1. The solid lines in FIG. 2 correspond to the visible contours of closure element 10, while the broken lines represent cut edges that are not visible in the perspective shown. FIG. 2A shows closure element 10 with wall 14 having the automatically closing slit-shaped indentation 141 with a central section 143. The cylindrical surfaces of the hollow cylinder are represented in FIG. 2A by the outermost solid line 200 and the broken line 202 offset toward the inside. FIG. 2B shows wall 12, opposite to wall 14. A circular central opening 121 is formed in wall 12.

FIG. 2B shows the alignment of opening 121 and central section 143 of slit-shaped indentation 141. Slit-shaped indentation 141 is shown as a partially broken line in FIG. 2B, because in the view selected there it is visible only inside opening 121.

Figure 3:
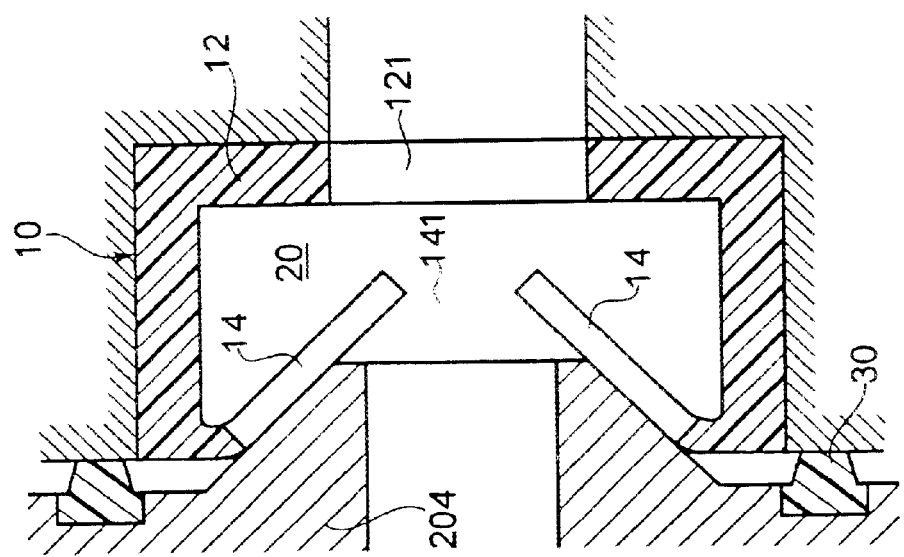
FIG. 3: is a longitudinal section through the closure element of FIG. 1, during a sterilization process.

FIG. 3 shows closure element 10 during a sterilization process. The connection of the sterilization device 204 is inserted from the left, as shown in FIG. 3, in such a way that it first touches wall 14. With further insertion, the device deforms the elastic wall 14 so that the slit-shaped indentation 141, which is closed when not in use, widens and forms an opening for the sterilization medium flowing in and out. The medium may be a liquid, gas or vapor. In the embodiment according to FIG. 3, a seal is formed by a sealing ring 30 on the sterilization device, forming a seal over the housing accommodating closure element 10.

A sterilization fluid can then pass through opening 141 into hollow space 20 of sealing element 10, and into the annular area which extends to gasket 30 in contact with the housing.

After liquid passes through slit-shaped indentation 141, which is deformed to create an opening, it goes through opening 121 into the part to be sterilized, for example into a dialysis filter. After removing the sterilization device 204 at the end of the sterilization, wall 14 of closure element 10 deforms back to its original shape, so the opening closes and forms again the slit-shaped indentation 141. Wall 14 then seals the sterilized part tightly, thus preventing leakage and dripping of sterilization liquid, and also preventing penetration of unwanted substances and microorganisms.

Figure 4:
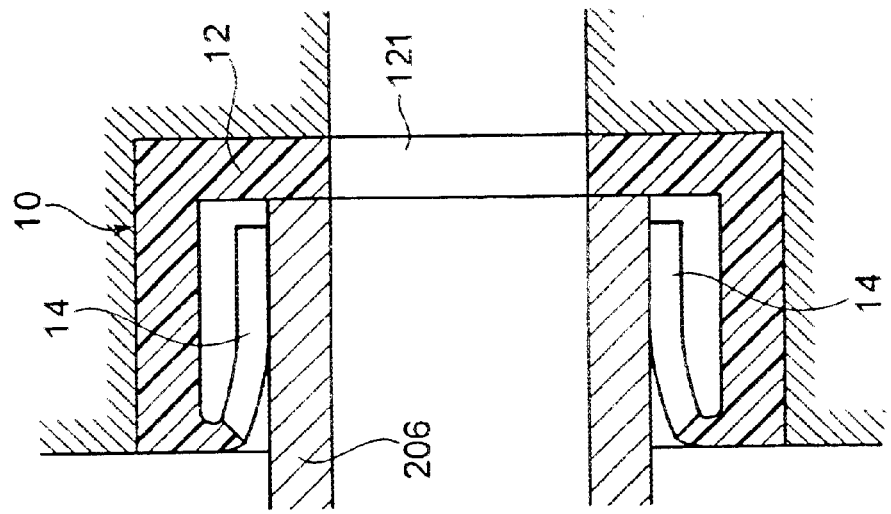
FIG. 4: is a longitudinal section through the closure element according to FIG. 1, during use to form a connection.

FIG. 4 shows the closure element 10 according to the invention during normal use. A connecting element 206 is inserted through the slit-shaped indentation 141 in wall 14 until the end side of the connection is in contact with the side of wall 12 adjacent to hollow space 20 of closure element 10. Depending on the diameter of the connecting element, the areas of wall 14 on both sides of slit-shaped indentation 141 can be curved in the direction of wall 12 as shown in FIG. 4. The fluid supplied and removed then passes through the opening of the connecting element and through opening 121 in wall 12, into and out of the connected part, which could be, for example, a connected dialysis filter. A tight and thus germ-proof connection is achieved due to the tight seal of the end side of the connecting element against the inside of wall 12. In addition, FIG. 4 illustrates how a linear passage for the liquid is obtained by aligning the connecting element 206 and closure element 10, thus largely preventing unwanted dead zones in the passage.

At the end of the treatment, the connecting element 206 can be retracted, so that the portions of wall 14 return to their original shape and again form a tightly sealed slit-shaped indentation 141, as illustrated in FIG. 2.

The embodiments illustrated in FIGS. 3 and 4 show that microorganisms can be prevented from passing through the connection during sterilization or during the normal use of closure element 10. Furthermore, closure element 10 can easily be removed from the corresponding housing recess 30, so that simple and inexpensive replacement is possible. Thus, a sterile and hygienic connection of the parts to be connected can be achieved, and contamination of the fluids conveyed can be prevented.

Figure 5:
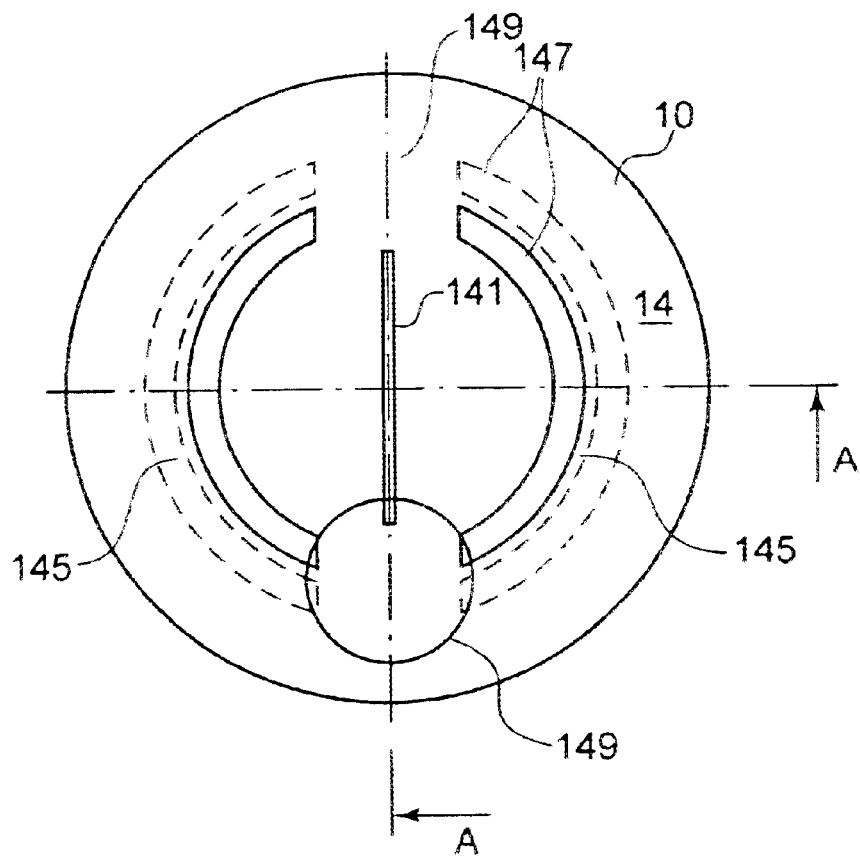
FIG. 5: is a top view of a closure element according to this invention having spring elements according to a second embodiment.
Figure 6:
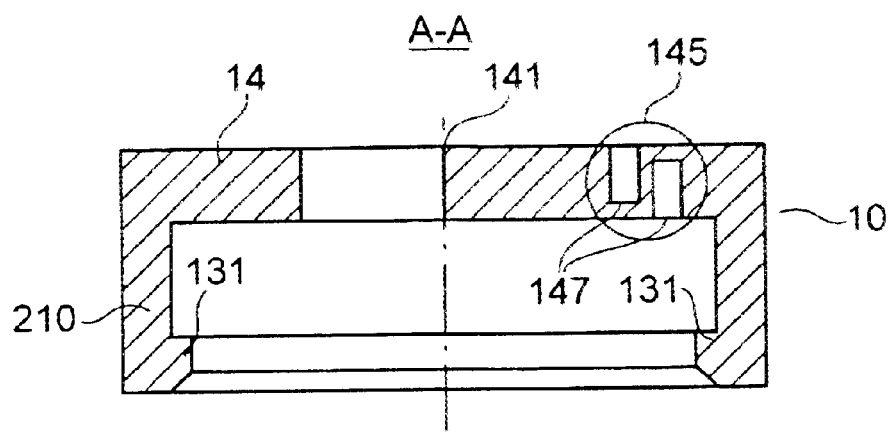
FIG. 6: is a longitudinal section on line A—A through the closure element as shown in FIG. 5, and FIG. 7: is a longitudinal section through the closure element according to this invention as shown in FIG. 5, immediately before being connected to a connecting element.
Figure 7:
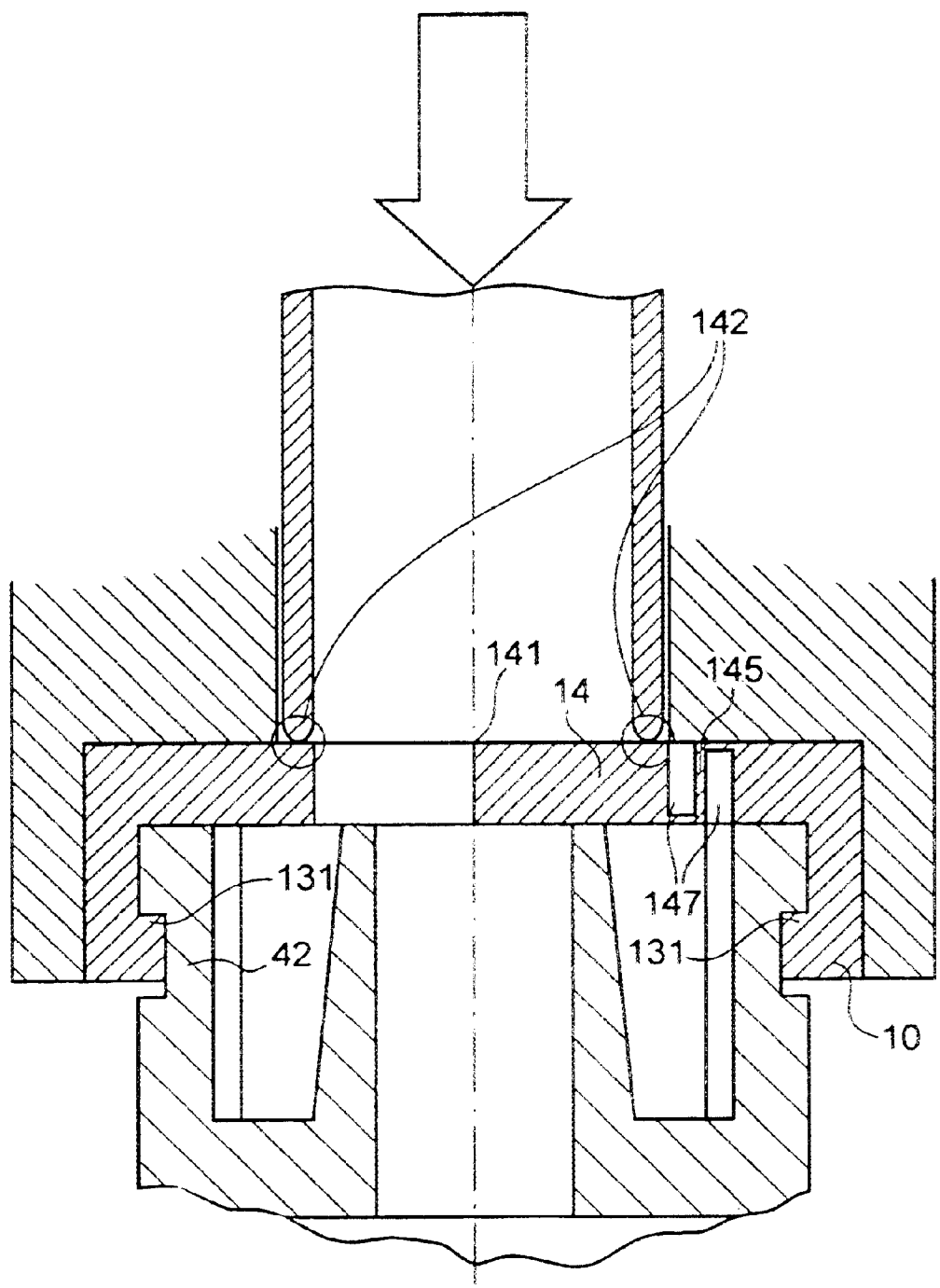

FIGS. 5 through 7 show a second embodiment of a closure element 10 according to this invention. FIG. 5 shows a top view of the second embodiment of closure element 10. Closure element 10 has a cylindrical shape, with an automatically closing slit-shaped indentation 141 in wall 14 being visible on the end face in FIG. 5. Spring elements 145 are arranged in the areas extending radially out to the right and left of slit-shaped indentation 141. The spring elements 145 can be, for example, grooves formed in wall 14, that enable wall 14 to flex in a spring-like manner. These spring elements thus serve to reduce the radial tension forces in a transverse direction to the path of the spring element by reducing the cross section of wall 14.

As shown in FIG. 6, spring element 145 according to the present embodiment comprises recesses 147 arranged alternatively in the top and bottom sides of wall 14. The recesses 147 reduce the cross-sectional area of wall 14, and lead to a desirable spring action and bending of wall 14.

FIG. 5 illustrates that spring elements 145 do not extend completely around the slit-shaped indentation 141 in wall 14, but instead extend only partially around it. In particular, spring elements 145 generally are not provided in area 149 which extends in the longitudinal direction of indentation 141. Due to this design, the acting radial force is increased in the closing direction, thus yielding an especially effective and germ-proof closure of indentation 141. Such a design of the closure element 10 with spring elements 145 thus leads to improved sealing properties of indentation 141 in wall 14.

Spring areas 145 may be incorporated in a closure element 10 made of silicone, according to the present embodiment, so that a pressure difference of ±0.25 bar can be tolerated without indentation 141 losing its sealing effect.

FIG. 6 also shows a cylindrical jacket 210 extending perpendicularly to wall 14, and serving as a fastening means with a peripheral projection 131 formed on its end area. Projection 131 serves to engage closure element 10 in a corresponding recess formed in a connecting element 42, shown in FIG. 7, and to secure it there reliably.

FIG. 7 shows a longitudinal section of the inserted closure element 10, according to the embodiment shown in FIGS. 5 and 6. Closure element 10 is placed on the projecting connecting element 42 and is locked by means of the peripheral projection 131.

If a pressure force, such as a force produced mechanically, pneumatically or hydraulically, is applied in the direction of the arrow in area 142 of wall 14, indentation 141 can be opened to a greater or lesser degree.

To ensure a sterile seal, it is necessary not only for slit-shaped indentation 141 in wall 14 to be sealed tightly, but also for a seal-tight connection to be established between closure element 10 and connecting element 42. This is achieved because closure element 10 includes a cylindrical surface forming the fastening means, designed to fit on the inside as well as the outside. As a result, the closure element 10 ensures through the inside surface a germ-proof seal with the outside surface of a projecting connecting element 42, and through the outside surface with the inside surface of a bushing-like connecting element.

What is claimed is:

1. A filter module having a plurality of connections for supplying or removing a fluid from a device, at least one of said connections comprising:
    a closure element;
    a wall formed in the closure element having an automatically closing slit-shaped indentation forming a germ-proof closure when closed; and
    means for fastening the closure element to a connecting element disposed adjacent to the wall.

2. The filter module according to claim 1, wherein the filter module is configured for one of dialysis, hemofiltration and ultrafiltration.

3. The filter module according to claim 1, wherein the closure element comprises one of an inside surface forming a germ-proof closure with the outside surface of the connecting element, and an outside surface forming a germ-proof closure with an inside surface of a bushing-like connection.

4. The filter module according to claim 1, wherein the closure element is substantially cylindrical, the fastening mean include a cylindrical surface, and the slit-shaped indentation is formed on a end face of the cylindrical closure element.

5. The filter module according to claim 1, wherein the closure element is symmetrical about an axis of the connection.

6. The filter module according to claim 1, wherein the slit-shaped indentation is in the shape of a cross or a star.

7. The filter module according to claim 1, further comprising a second wall opposite to the wall having the indentation, the second wall having an opening for passage of a fluid.

8. The filter module according to claim 7, wherein a middle portion of the indentation is aligned with the opening.

9. The filter module according to claim 7, further comprising a surface extending around the opening in the second wall, the surface lying in a plane substantially perpendicular to a joining direction of the closure element to the connecting element.

10. The filter module according to claim 1, wherein the closure element is formed of one piece.

11. The filter module according to claim 1, wherein the wall and the closure element are made of plastic.

12. The filter module according to claim 11, wherein the plastic is silicone.

13. The filter module according to claim 1, wherein the wall comprises a spring element acting in a radial direction.

14. The filter module according to claim 1, wherein the slit-shaped indentation forms a germ-proof closure adapted to withstand a pressure difference up to about ±0.25 bar.

* * * * *